United States Patent
Mori et al.

(10) Patent No.: US 10,365,335 B2
(45) Date of Patent: Jul. 30, 2019

(54) MAGNETIC RESONANCE IMAGING APPARATUS, RECEIVING COIL, COUCH, AND RELAY DEVICE

(71) Applicant: TOSHIBA MEDICAL SYSTEMS CORPORATION, Otawara-shi (JP)

(72) Inventors: Akio Mori, Tochigi (JP); Mitsuo Takagi, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1176 days.

(21) Appl. No.: 14/632,183

(22) Filed: Feb. 26, 2015

(65) Prior Publication Data
US 2015/0168513 A1 Jun. 18, 2015

Related U.S. Application Data (63) Continuation of application No. PCT/JP2013/073231, filed on Aug. 29, 2013.

(30) Foreign Application Priority Data

Aug. 29, 2012 (JP) ................................ 2012-189090

(51) Int. Cl.
*G01R 33/36* (2006.01)
*A61B 5/055* (2006.01)
(Continued)

(52) U.S. Cl.
CPC .............. *G01R 33/36* (2013.01); *A61B 5/055* (2013.01); *G01R 33/30* (2013.01); *G01R 33/34* (2013.01);
(Continued)

(58) Field of Classification Search
CPC ........ G01R 33/30; G01R 33/34; G01R 33/36; G01R 33/3621; A61B 5/055
See application file for complete search history.

(56) References Cited

U.S. PATENT DOCUMENTS

| 4,689,563 A | * | 8/1987 | Bottomley | ......... G01R 33/3607 324/309 |
| 5,461,314 A | * | 10/1995 | Arakawa | ............ G01R 33/3628 324/318 |

(Continued)

FOREIGN PATENT DOCUMENTS

| JP | 5-130978 | 5/1993 |
| JP | 2001-224572 | 8/2001 |

(Continued)

OTHER PUBLICATIONS

International Search Report for PCT/JP2013/073231, dated Oct. 1, 2013, two pages.
(Continued)

*Primary Examiner* — Dixomara Vargas
(74) *Attorney, Agent, or Firm* — Nixon & Vanderhye P.C.

(57) ABSTRACT

According to an embodiment, a magnetic resonance imaging apparatus includes a couch, a gantry, a receiving coil, a converter, and a collector. On the couch, a subject is placed. The gantry supports a static magnetic field magnet and a gradient coil. The receiving coil receives a magnetic resonance signal emitted from the subject. The converter converts a magnetic resonance signal output from the receiving coil into a digital signal, thereby generating magnetic resonance signal data. The collector collects the magnetic resonance signal data. The couch or the gantry includes a coil port that connects the receiving coil and the collector to each other. The converter is provided in the coil port or a relay device that relays between the receiving coil and the coil port.

9 Claims, 9 Drawing Sheets

(51) Int. Cl.
  *G01R 33/30* (2006.01)
  *G01R 33/34* (2006.01)
  *A61B 5/00* (2006.01)
  *G01R 33/341* (2006.01)

(52) U.S. Cl.
  CPC ........ *G01R 33/3621* (2013.01); *A61B 5/0555* (2013.01); *A61B 5/7203* (2013.01); *G01R 33/341* (2013.01)

(56) References Cited

U.S. PATENT DOCUMENTS

| | | | | |
|---|---|---|---|---|
| 5,483,158 A | * | 1/1996 | van Heteren | G01R 33/3628 324/318 |
| 5,565,779 A | * | 10/1996 | Arakawa | G01R 33/3628 324/318 |
| 6,291,994 B1 | * | 9/2001 | Kim | G01R 33/441 324/300 |
| 7,378,844 B2 | | 5/2008 | Watkins et al. | |
| 7,408,352 B2 | * | 8/2008 | Bittner | A61B 5/0555 324/318 |
| 7,486,982 B2 | * | 2/2009 | Branch | G01R 33/422 324/318 |
| 7,490,377 B2 | * | 2/2009 | Ahlman | A61B 6/0442 5/613 |
| 7,777,494 B2 | | 8/2010 | Dooms et al. | |
| 7,784,121 B2 | * | 8/2010 | Ahlman | A61B 6/0442 5/613 |
| 7,869,858 B2 | * | 1/2011 | Calderon | A61G 7/1034 378/62 |
| 8,046,851 B2 | * | 11/2011 | Ahlman | A61B 6/0442 5/613 |
| 9,301,707 B2 | * | 4/2016 | Dahan | G01R 33/3802 |
| 9,549,687 B2 | * | 1/2017 | Georgiev | A61B 5/0555 |

FOREIGN PATENT DOCUMENTS

| | | |
|---|---|---|
| JP | 2003-210432 | 7/2003 |
| JP | 2005-270261 | 10/2005 |
| JP | 2009-518098 | 5/2009 |
| JP | 2012-081013 | 4/2012 |
| WO | WO 2009/139287 | 11/2009 |

OTHER PUBLICATIONS

Non-English Written Opinion of the ISA for PCT/JP2013/073231, dated Oct. 1, 2013, three pages.

Japanese office action dated Feb. 13, 2018, in Patent Application No. JP 2013-178689.

* cited by examiner

MAGNETIC RESONANCE IMAGING APPARATUS, RECEIVING COIL, COUCH, AND RELAY DEVICE

CROSS-REFERENCE TO RELATED APPLICATIONS

This application is a continuation of PCT international application Ser. PCT/JP2013/073231, filed on Aug. 29, 2013 which designates the United States, and which claims the benefit of priority from Japanese Patent Application No. 2012-189090, filed on Aug. 29, 2012; the entire contents of which are incorporated herein by reference.

FIELD

Embodiments described herein relate generally to a magnetic resonance imaging apparatus, a receiving coil, a couch, and a relay device.

BACKGROUND

Conventionally, a magnetic resonance imaging apparatus includes a receiving coil that receives a magnetic resonance signal emitted from a subject to be tested, a receiver that generates magnetic resonance signal data by converting the magnetic resonance signal output from the receiving coil into a digital signal, and a collector that collects the magnetic resonance signal data. In such a configuration, conversion of the magnetic resonance signal received by the receiving coil into a digital signal at as early a stage as possible to suppress inclusion of noise in the magnetic resonance signal is recently considered.

DETAILED DESCRIPTION

According to an embodiment, a magnetic resonance imaging apparatus includes a couch, a gantry, a receiving coil, a converter, and a collector. On the couch, a subject is placed. The gantry supports a static magnetic field magnet and a gradient coil. The receiving coil receives a magnetic resonance signal emitted from the subject. The converter converts a magnetic resonance signal output from the receiving coil into a digital signal, thereby generating magnetic resonance signal data. The collector collects the magnetic resonance signal data. The couch or the gantry includes a coil port that connects the receiving coil and the collector to each other. The converter is provided in the coil port or a relay device that relays between the receiving coil and the coil port.

First Embodiment

Figure 1:
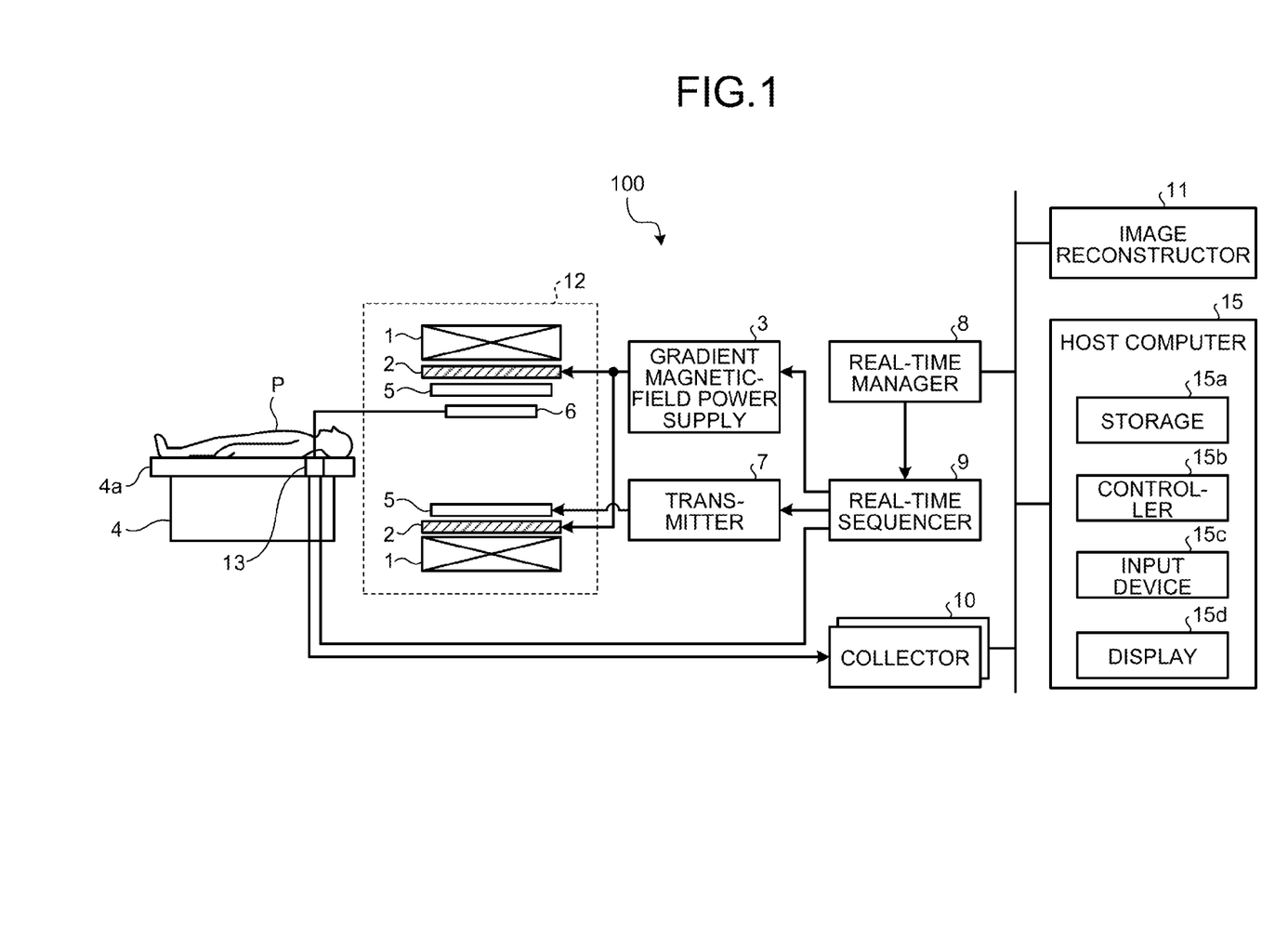
FIG. 1 is a block diagram of a configuration example of a magnetic resonance imaging (MRI) apparatus according to a first embodiment.

FIG. 1 is a block diagram of a configuration example of an MRI apparatus 100 according to a first embodiment.

A static magnetic field magnet 1 is formed in a hollow cylindrical shape and generates a uniform static magnetic field in the internal space. The static magnetic field magnet 1 is, for example, a permanent magnet or a superconducting magnet. A gradient coil 2 is formed in a hollow cylindrical shape and generates a gradient magnetic field in the internal space. Specifically, the gradient coil 2 is placed within the static magnetic field magnet 1 and generates a gradient magnetic field upon receipt of supply of a current from a gradient magnetic-field power supply 3. The gradient magnetic-field power supply 3 supplies a current to the gradient coil 2 according to pulse-sequence execution data transmitted from a real-time sequencer 9. The static magnetic field magnet 1 and the gradient coil 2 are supported by a gantry 12.

A couch 4 includes a couchtop 4a on which a subject P is placed and the couchtop 4a is inserted into a hollow (an imaging opening) of the gradient coil 2 with the subject P being placed on the couchtop 4a. The couch 4 is usually installed in such a manner that the longitudinal direction thereof is parallel to the central axis of the static magnetic field magnet 1. The couch 4 includes coil ports 13 that connect a receiving coil 6 to collectors 10.

Figure 2:
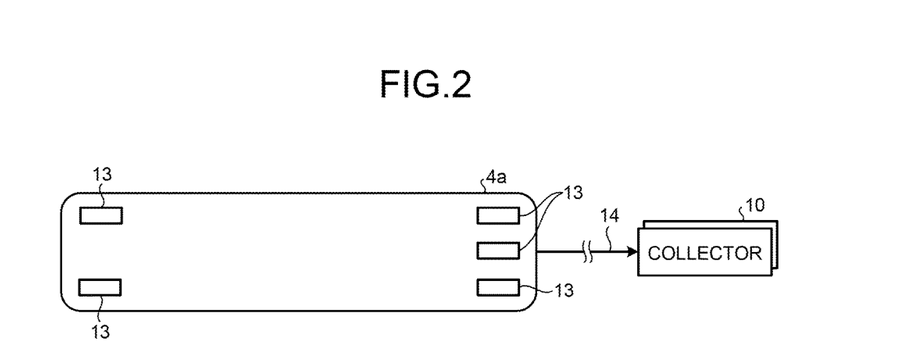
FIG. 2 is an arrangement example of coil ports according to the first embodiment.

FIG. 2 is an arrangement example of the coil ports 13 according to the first embodiment. As shown in FIG. 2, the coil ports 13 are arranged, for example, near ends in the longitudinal direction of the couchtop 4a included in the couch 4. While a case where two coil ports 13 are arranged near one of the ends of the couchtop 4a and three coil ports 13 are arranged near the other end is shown in FIG. 2, the positions and the number of the coil ports 13 are not limited thereto.

In the first embodiment, each of the coil ports 13 includes an A/D converter that converts a magnetic resonance signal output from the receiving coil 6 into a digital signal to generate magnetic resonance signal data. Each of the coil ports 13 transmits the magnetic resonance signal data to the corresponding collector 10. In this case, the A/D converter converts the generated magnetic resonance signal data into an optical signal and outputs the optical signal. The magnetic resonance signal data of the optical signal output from the A/D converter is multiplexed, for example, by an optical multiplexer provided in the couch 4 and is transmitted to the corresponding collector 10 via an optical cable 14. The A/D converter provided in each of the coil ports 13 is explained in detail later.

The couch 4 can be a fixed couch that is fixed to the gantry 12 or a mobile couch (also referred to as "dockable couch") that can be detached from the gantry 12. For example, the mobile couch includes a moving device such as wheels so that the subject can be moved from outside of an imaging room where the MRI apparatus 100 is placed to the inside of the imaging room, or from the inside of the imaging room to outside thereof.

Figure 3:
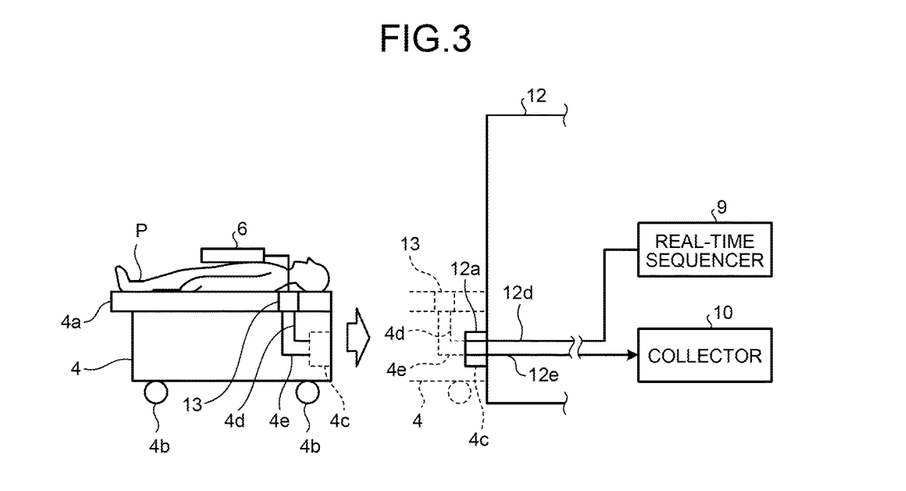
FIG. 3 is an example where a couch according to the first embodiment is a mobile couch.

FIG. 3 is an example where the couch 4 according to the first embodiment is a mobile couch. For example, as shown in FIG. 3, the mobile couch 4 includes wheels 4b for moving. The couch 4 also includes a to-be-fixed part 4c that engages with a fixing part 12a provided on the gantry 12. For example, the to-be-fixed part 4c of the couch 4 is connected to each of the coil ports 13 via a real-time-sequencer cable 4d and a collector cable 4e. The fixing part 12a of the gantry 12 is connected to the real-time sequencer 9 via a real-time-sequencer cable 12d and is connected to the collectors 10 via collector cables 12e. In this case, the collector cables 4e and 12e are, for example, optical cables.

As shown by broken lines in FIG. 3, when the to-be-fixed part 4c of the couch 4 engages with the fixing part 12a of the gantry 12, the couch 4 is mechanically fixed to the gantry 12 as well as the cables 4d of the couch 4 and the real-time-sequencer cable 12d of the gantry 12 are electrically connected to each other and the collector cables 4e of the couch 4 and the collector cables 12e of the gantry 12 are electrically connected to each other. Accordingly, the receiving coil 6 connected to the coil ports 13 is electrically connected to the real-time sequencer 9 and the collectors 10.

Referring back to FIG. 1, a transmitting coil 5 generates a high-frequency magnetic field. Specifically, the transmitting coil 5 is placed within the gradient coil 2 and generates a high-frequency magnetic field upon receipt of supply of a high-frequency pulse from a transmitter 7. The transmitter 7 transmits a high-frequency pulse corresponding to a Larmor frequency to the transmitting coil 5 according to the pulse-sequence execution data transmitted from the real-time sequencer 9.

The receiving coil 6 receives the magnetic resonance signal emitted from the subject P. Specifically, the receiving coil 6 receives the magnetic resonance signal emitted from the subject P under an influence of the high-frequency magnetic field. The receiving coil 6 amplifies the received magnetic resonance signal with an internal preamplifier and outputs the amplified magnetic resonance signal to the A/D converters of the coil ports 13 provided on the couchtop 4a of the couch 4. For example, the receiving coil 6 is a head receiving coil, a spine receiving coil, or an abdomen receiving coil. In the first embodiment, the receiving coil 6 is an array coil including a plurality of coil elements and outputs the magnetic resonance signals received by these coil elements through a plurality of channels.

A real-time manager 8 controls the real-time sequencer 9 according to an imaging condition instructed by an operator. Specifically, the real-time manager 8 analyzes an imaging condition transmitted from a host computer 15, generates pulse-sequence execution data, and transmits the generated pulse-sequence execution data to the real-time sequencer 9.

The real-time sequencer 9 is connected to the gradient magnetic-field power supply 3, the transmitter 7, and the A/D converters of the coil ports 13 and controls input/output of data transmitted/received between the connected components and the host computer 15. Specifically, the real-time sequencer 9 controls the gradient magnetic-field power supply 3, the transmitter 7, and the A/D converters of the coil ports 13 to execute a pulse sequence defined according to the imaging condition based on the pulse-sequence execution data transmitted from the real-time manager 8.

The collectors 10 collect the magnetic resonance signal data generated by the A/D converters provided in the coil ports 13, respectively. Upon collection of the magnetic resonance signal data, the collectors 10 each perform a correction process such as an averaging process or a phase correction process for the collected magnetic resonance signal data and transmit the corrected magnetic resonance signal data to an image reconstructor 11. The MRI apparatus 100 includes a plurality of the collectors 10 corresponding to the coil ports 13 provided on the couch 4, respectively.

The image reconstructor 11 performs image treatment such as a filtering process or a reconstruction process for the magnetic resonance signal data transmitted from the collectors 10 to generate image data. Specifically, the image reconstructor 11 reconstructs two-dimensional or three-dimensional image data by performing image treatment such as a k-space-conversion filtering process, two-dimensional or three-dimensional FFT (Fast Fourier Transform), or image filtering and transmits the reconstructed image data to the host computer 15.

The host computer 15 includes a storage 15a, a controller 15b, an input device 15c, and a display 15d. According to a receiving coil selected by the operator through the input device 15c, the host computer 15 transmits information indicating which collector stores each of channels of the selected receiving coil in a buffer memory thereof and a selection signal indicating one of the channels in the selected receiving coil to be selected for use of imaging, to the real-time sequencer 9 via the real-time manager 8.

The controller 15b controls the components mentioned above, thereby controlling the MRI apparatus 100 as a whole. For example, the controller 15b includes a CPU (Central Processing Unit). The input device 15c receives an imaging instruction or the like from the operator. The display 15d displays image data or the like.

In one embodiment, for example, one or a plurality of the real-time manager 8, real-time sequencer 9, collector 10, image reconstructor 11, and controller 15b includes a processor such as a CPU or MPU (Micro Processing Unit), and a memory. The memory stores processor-executable instructions that, when executed by the processor, cause the processor to perform the processes that is to be performed by the real-time manager 8, real-time sequencer 9, collector 10, image reconstructor 11, or controller 15b.

In the first embodiment, with this configuration, the coil ports 13 each include the A/D converter that converts the magnetic resonance signal output from the receiving coil 6 into a digital signal to generate the magnetic resonance signal data as mentioned above.

Figure 4:
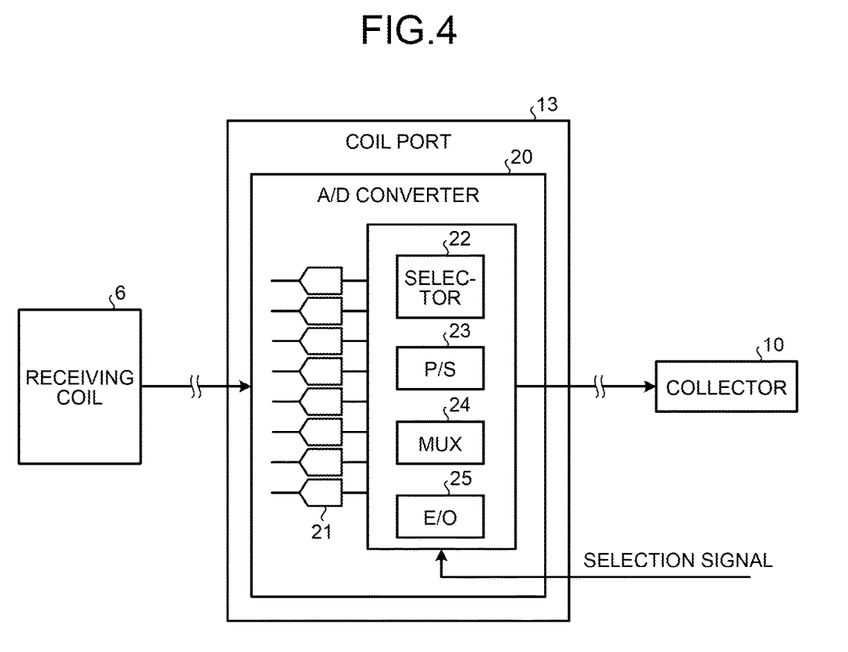
FIG. 4 is a block diagram of a configuration example of an A (Analog)/D (Digital) converter according to the first embodiment.

FIG. 4 is a block diagram of a configuration example of an A/D converter 20 according to the first embodiment. As shown in FIG. 4, the A/D converter 20 is provided in each of the coil ports 13 and converts the magnetic resonance signal output from the receiving coil 6 into a digital signal to generate the magnetic resonance signal data and transmits the generated magnetic resonance signal data to the corresponding collector 10.

Specifically, the A/D converter 20 has a function to convert the magnetic resonance signal into a digital signal by a direct sampling method to generate the magnetic resonance signal data. The A/D converter 20 converts the magnetic resonance signal into a digital signal to generate the magnetic resonance signal data with respect to each of the channels of the receiving coil 6.

For example, as shown in FIG. 4, the A/D converter 20 includes a plurality of ADCs 21, a selector 22, a parallel/serial (P/S) converter 23, a multiplexer (MUX) 24, and an electrical/optical (E/O) converter 25. In the example shown in FIG. 4, a case where the magnetic resonance signal is output from the receiving coil 6 through eight channels is shown.

Each of the ADCs 21 converts an analog magnetic resonance signal output from the receiving coil 6 into a digital signal to generate the magnetic resonance signal data. Specifically, each of the ADCs 21 is an ADC for the direct sampling method and directly samples the analog magnetic resonance signal output from the receiving coil 6 to convert the signal into a digital signal. Each of the ADCs 21 then transmits the digitalized magnetic resonance signal as the magnetic resonance signal data to the selector 22.

In this case, as many ADCs 21 as channels of the receiving coil 6 are provided. Because the ADCs for the direct sampling method generally have a simplified configuration, the integration degree thereof can be easily increased and thus many ADCs can be incorporated in each of the coil ports 13. In the example shown in FIG. 4, because the receiving coil 6 includes eight channels, eight ADCs 21 are provided. Accordingly, the magnetic resonance signal data with respect to each of the eight channels of the receiving coil 6 is transmitted to the selector 22. The number of ADCs 21 is not limited to eight and a single ADC 21 or a plurality of ADCs 21 can be provided according to the number of channels in the receiving coil.

The selector 22 selects magnetic resonance signal data of at least one channel among the magnetic resonance signal data generated with respect to the channels, respectively. Specifically, the selector 22 obtains a selection signal indicating a channel selected for use of imaging from the real-time sequencer 9, identifies the selected channel based on the obtained selection signal, and transmits the magnetic resonance signal data of the identified channel to the P/S converter 23.

The P/S converter 23 converts the magnetic resonance signal data from a parallel signal to a serial signal. Specifically, the P/S converter 23 converts the magnetic resonance signal data transmitted from the selector 22 with respect to each channel from a parallel signal to a serial signal and transmits the converted magnetic resonance signal data to the MUX 24.

The MUX 24 multiplexes the magnetic resonance signal data generated with respect to the channels. Specifically, the MUX 24 multiplexes the magnetic resonance signal data with respect to the channels transmitted from the P/S converter 23 and transmits the multiplexed magnetic resonance signal data to the E/O converter 25.

The E/O converter 25 converts the magnetic resonance signal data to an optical signal. Specifically, the E/O converter 25 converts the magnetic resonance signal data transmitted from the MUX 24 from an electrical signal to an optical signal and transmits the converted magnetic resonance signal data to the corresponding collector 10.

As mentioned above, according to the first embodiment, each of the A/D converters 20 that convert the magnetic resonance signal output from the receiving coil 6 into a digital signal to generate the magnetic resonance signal data is provided to each of the coil ports 13 on the couch 4. When the A/D converter 20 is provided in each of the coil ports 13 on the couch 4 in this way, A/D conversion is performed at a time when the magnetic resonance signal output from the receiving coil 6 is input to each of the coil ports 13 and thus the magnetic resonance signal is digitalized at an early stage on a path from the receiving coil 6 to the corresponding collector 10. Therefore, inclusion of noise in the magnetic resonance signal can be suppressed.

Conventionally, there is an MRI apparatus that includes as many ADCs as minimum channels required in a receiver at a later stage and collects magnetic resonance signal data. In such an MRI apparatus, however, only a smaller number of channels than the number of receiving coils that are concurrently connectable and the number of channels in the receiving coils can be included because the receiver is costly. Therefore, for example, a selection circuit that selects 32 channels from among 128 channels is generally provided at the previous stage of the receiver. In this case, the selection circuits having different constants need to be provided according to magnetic field strengths or signal isolation among the channels needs to be considered, which leads to great restrictions in design. Furthermore, setting on the selection circuits is complicated and thus the operator cannot easily select a receivable port.

To solve these problems, a system of providing ADCs in receiving coils is conventionally used. In this system, however, it is difficult to install the ADCs compactly due to hardware restrictions. Therefore, in some cases, the receiving coils themselves are increased in sizes or interference among the receiving coils needs to be considered in designing according to various connection states of the receiving coils, resulting in costly receiving coils.

In contrast thereto, according to the first embodiment, A/D conversion of the magnetic resonance signal is performed in the coil ports and thus no receiver is required at the later stage. Therefore, inclusion of noise in the magnetic resonance signal can be suppressed with a simple configuration. Furthermore, with elimination of the receiver at the later stage, the selection circuit can be also eliminated and thus the magnetic resonance signals output from all the receiving coils that are concurrently connectable and from all channels of the receiving coils can be transmitted to the collectors. Accordingly, the magnetic resonance signals can be collected more efficiently.

Furthermore, in the first embodiment, manufacturing costs of the apparatus can be reduced by using inexpensive ADCs for the direct sampling method. As mentioned above, because the ADCs for the direct sampling method generally have a simplified configuration, the integration degree thereof can be easily increased and many ADCs can be incorporated in each of the coil ports 13.

Figure 5:
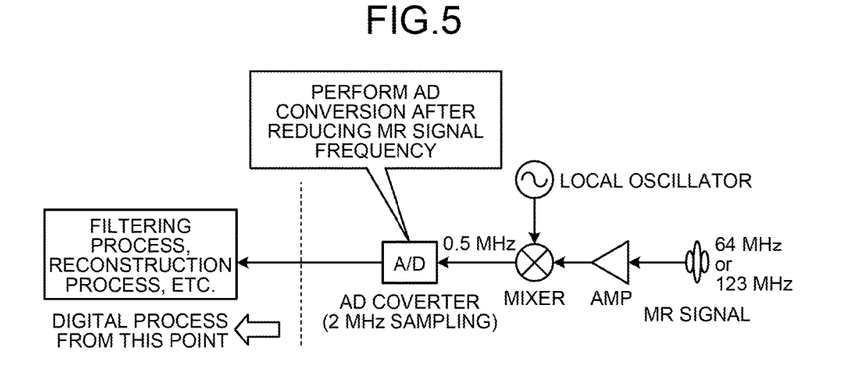
FIG. 5 is an example of a receiving circuit using a conventional ADC (Analog Digital Converter)

FIG. 5 is an example of a receiving circuit using a conventional ADC. As shown in FIG. 5, in a configuration using the conventional ADC, for example, after a magnetic resonance (MR) signal received by a receiving coil is amplified by a high-frequency amplifier (AMP), the frequency thereof is reduced by a local oscillator and a mixer, and then A/D conversion is performed by the ADC. Therefore, the circuit has a large scale and is difficult to mount on a couch.

Figure 6:
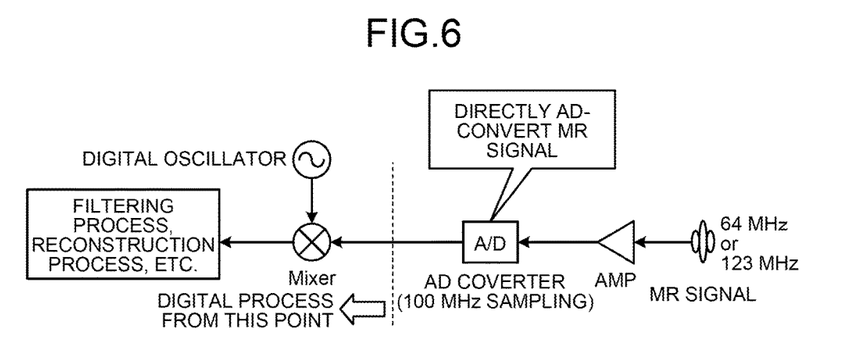
FIG. 6 depicts a configuration of a receiving circuit using an ADC for direct sampling according to the first embodiment.

FIG. 6 depicts a configuration of a receiving circuit using the ADC for direct sampling according to the first embodiment. As shown in FIG. 6, in the first embodiment, for example, after an MR signal received by a receiving coil is amplified by a high-frequency AMP, the MR signal is directly sampled using the ADC for the direct sampling method, thereby performing A/D conversion. In this way, in the configuration using the ADC for direct sampling method, the circuit has a smaller scale than in the configuration using the conventional ADC and therefore as many ADCs as channels can be easily mounted. In the example shown in FIG. 6, after the MR signal is digitalized by the ADC, a thinning process is performed by a digital oscillator and a mixer. After having been digitalized, the thinning process or a decimation process can be easily performed for the MR signal.

Second Embodiment

A second embodiment is explained next. In the first embodiment, a case where the A/D converter 20 is provided in each of the coil ports 13 on the couch 4 is explained. In the second embodiment, a case where the A/D converter is provided on a path from the receiving coil 6 to each of the coil ports 13 is explained.

While an MRI apparatus according to the second embodiment has basically the same configuration as that of the MRI apparatus 100 shown in FIG. 1, the A/D converter 20 is not provided in each of the coil ports 13 on the couch 4. A case where the MRI apparatus 100 includes a relay device that relays between the receiving coil 6 and the coil ports 13 on the couch 4 and where an A/D converter is provided in the relay device is explained as an example in the second embodiment. In the second embodiment, constituent elements having functions identical to those of the elements described in the first embodiment are denoted by like reference signs and explanations thereof will be omitted.

Figure 7:
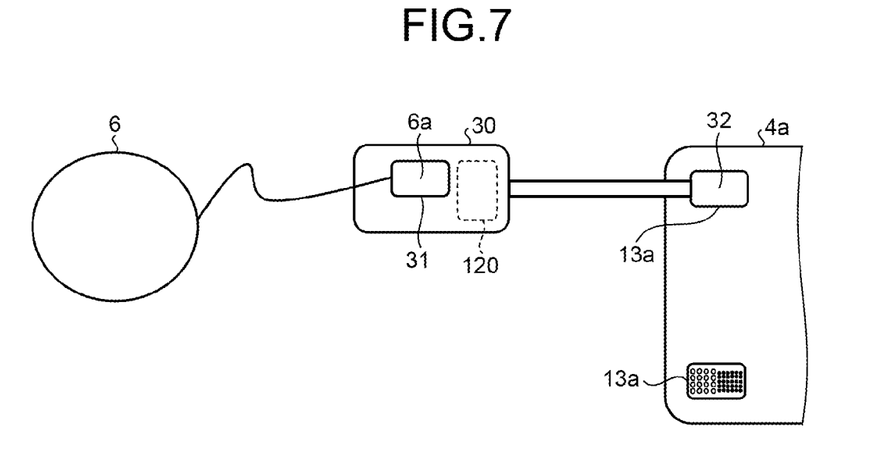
FIG. 7 depicts a relay device according to a second embodiment.

FIG. 7 depicts a relay device 30 according to the second embodiment. As shown in FIG. 7, the relay device 30 includes an A/D converter 120. While having the same function as that of the A/D converter 20 explained in the first embodiment, the A/D converter 120 is different from the A/D converter 20 in outputting multiplexed magnetic resonance signal data as an electrical signal.

The relay device 30 includes an input connector 31 and an output connector 32. The input connector 31 inputs the magnetic resonance signal from the receiving coil 6. Specifically, the input connector 31 is connected to an output connector 6a of the receiving coil 6 and outputs the magnetic resonance signal input from the receiving coil 6 to the A/D converter 120. The output connector 32 outputs magnetic resonance signal data generated by the A/D converter 120 to the coil ports 13 provided on the couchtop 4a of the couch 4. Specifically, the output connector 32 is connected to input connectors 13a of the coil ports 13 and outputs the magnetic resonance signal data output from the A/D converter 120 to the coil ports 13.

The input connector 31 of the relay device 30 has the same shape as that of the input connectors 13a of the coil ports 13 on the couch 4. The output connector 32 of the relay device 30 has the same shape as that of the output connector 6a of the receiving coil 6.

Figure 8:
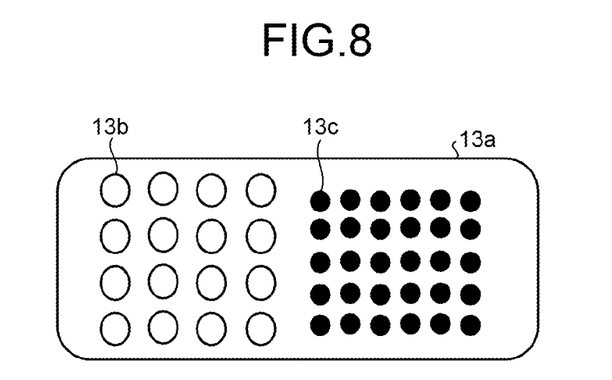
FIG. 8 is an example of an input connector of a coil port according to the second embodiment.

FIG. 8 is an example of the input connector 13a of the coil port 13 according to the second embodiment. As shown in FIG. 8, for example, the input connector 13a of the coil port 13 includes a plurality of MRI signal terminals 13b arrayed in four rows and four columns and a plurality of coil information terminals 13c arrayed in five rows and six columns. The MRI signal terminals 13b are terminals for inputting the magnetic resonance signal data to the coil port 13. For example, the MRI signal terminals 13b are BNC (Bayonet Neill Concelman) connectors or coaxial connectors. The coil information terminals 13c are terminals for inputting a coil ID for uniquely identifying the receiving coil 6 to the coil port 13. In the second embodiment, the input connector 31 of the relay device 30 also includes a plurality of MRI signal terminals arrayed in four rows and four columns and a plurality of coil information terminals arrayed in five rows and six columns as the input connector 13a shown in FIG. 8.

In this way, in the second embodiment, the input connector 31 of the relay device 30 has the same shape as that of the input connectors 13a of the coil ports 13 on the couch 4 and the output connector 32 of the relay device 30 has the same shape as that of the output connector 6a of the receiving coil 6. That is, the relay device 30 can be inserted between the receiving coil 6 and the coil ports 13 which are conventionally used.

Therefore, according to the second embodiment, with use of the relay device 30, an analog magnetic resonance signal can be converted into a digital signal on paths from the receiving coil 6 to the coil ports 13 even when the coil ports 13 include no A/D converter. That is, an analog magnetic resonance signal can be converted into a digital signal on the paths from the receiving coil 6 to the coil ports 13 without altering specifications of the conventional receiving coil and the conventional couch. When the receiving coil 6 is connected to all the coil ports 13 via the relay device 30, the conventional costly receiver mentioned above is not required and thus the manufacturing costs of the apparatus can be reduced while using the conventional couch.

A case where the input connector 31 of the relay device 30 has the same shape as the input connectors 13a of the coil ports 13 on the couch 4 and the output connector 32 of the relay device 30 has the same shape as the output connector 6a of the receiving coil 6 has been explained in this case as an example. With this configuration, the relay device 30 can be introduced without changing the receiving coil and the couch which are already installed and used in hospitals and the like. However, the shapes of the input connector 31 and the output connector 32 of the relay device 30 are not limited to this example.

For example, a receiving coil and a relay device can be newly introduced without changing the couch already used. In such a case, it suffices to provide the output connector of the relay device with a shape connectable to the input connectors of the coil ports on the already-used couch and to provide the input connector of the relay device with a shape connectable to the output connector of the new receiving coil. Alternatively, a couch and a relay device can be newly introduced without changing the receiving coil already used. In such a case, it suffices to provide the input connector of the relay device with a shape connectable to the output connector of the already-used receiving coil and to provide the output connector of the relay device with a shape connectable to the input connectors of the coil ports on the new couch.

For example, a skip circuit that skips A/D conversion can be provided for each of the coil ports 13 on the couch 4 to address both of a case where the relay device 30 is used and a case where the relay device 30 is not used. This skip circuit can be provided, for example, in the couch 4 or the gantry 12.

Figure 9:
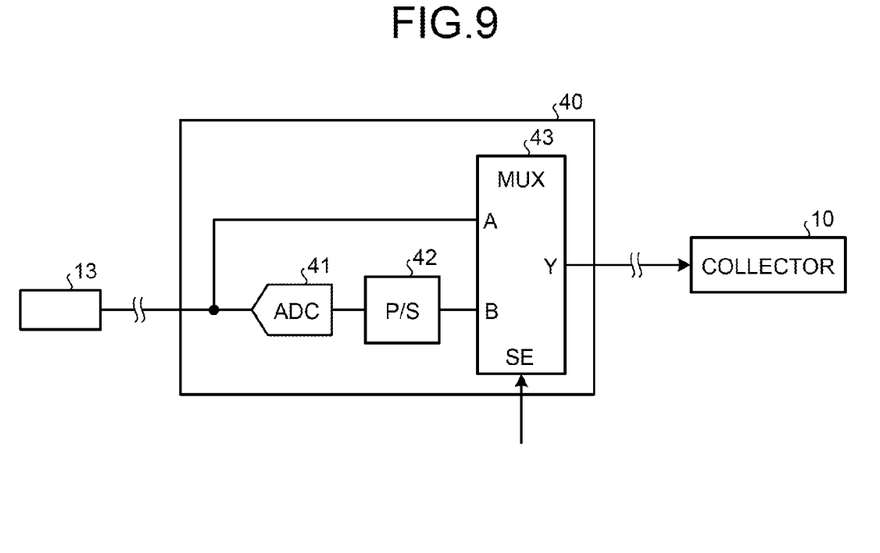
FIG. 9 is an example of a skip circuit according to the second embodiment.

FIG. 9 is an example of a skip circuit 40 according to the second embodiment. As shown in FIG. 9, the skip circuit 40 includes, for example, an ADC 41, a P/S converter 42, and a data selection circuit (MUX) 43. The skip circuit 40 receives a magnetic resonance signal or magnetic resonance signal data from the corresponding coil port 13. That is, when the conventional receiving coil including no A/D conversion function is directly connected to the coil port 13, the skip circuit 40 receives an analog magnetic resonance signal from the coil port 13. When the receiving coil is connected to the coil port 13 via the relay device 30, the skip circuit 40 receives digital magnetic resonance signal data from the coil port 13.

The magnetic resonance signal or the magnetic resonance signal data input to the skip circuit 40 is supplied to an input A of the data selection circuit 43 and an input of the ADC 41. The ADC 41 converts the input magnetic resonance signal into a digital signal and outputs the digital signal to the P/S converter 42. The P/S converter 42 converts the input digital signal into a serial signal and supplies the serial signal to an input B of the data selection circuit 43. The data selection circuit 43 outputs a signal input through any one of the inputs A and B from an output Y based on a selection control signal SE. The signal output from the data selection circuit 43 is transmitted to the corresponding collector 10 as an output signal of the skip circuit 40.

For example, a signal "0" is input to the data selection circuit 43 when the receiving coil is directly connected to the coil port 13 and a signal "1" is input thereto when the receiving coil is connected to the coil port 13 via the relay device 30. When the selection control signal SE is the signal "0", the data selection circuit 43 outputs a signal input through the input B from the output Y. In this case, the magnetic resonance signal converted into a digital signal by the ADC 41, that is, the magnetic resonance signal data is output from the output Y. When the selection control signal SE is the signal "1", the data selection circuit 43 outputs a signal input through the input A from the output Y. In this case, the digital magnetic resonance signal data input through the coil port 13 is output from the output Y. That is, under this control, the digital magnetic resonance signal data is output from the skip circuit 40 in any of these cases. Inputting of the selection control signal SE can be performed manually by the operator or automatically based on IDs attached to the receiving coil and the relay device 30.

As described above, both of the case where the relay device 30 is used and the case where the relay device 30 is not used can be addressed using the skip circuit 40. By providing the skip circuit 40 for each of the coil ports 13, the digital magnetic resonance signal data can be transmitted to the collector 10 corresponding to each of the coil ports 13 even when the coil ports 13 to which the receiving coil 6 is connected via the relay device 30 and the coil ports 13 to which the receiving coil 6 is connected without the relay device 30 are mixed.

Third Embodiment

A third embodiment is explained next. In the first embodiment, the case where the magnetic resonance signal data is transmitted to the collectors 10 with respect to the corresponding coil ports 13 on the couch 4, respectively, is explained. In the third embodiment, a case where magnetic resonance signal data output from one coil port 13 is distributed to plural collectors is explained.

While having basically the same configuration as that of the MRI apparatus 100 shown in FIG. 1, an MRI apparatus according to the third embodiment further includes a distribution substrate between the coil ports 13 and the collectors 10. In the third embodiment, an A/D converter included in each of the coil ports 13 does not multiplex the magnetic resonance signal data and outputs the data with respect to each channel. In the third embodiment, constituent elements having functions identical to those of the elements described in the first embodiment are denoted by like reference signs and explanations thereof will be omitted.

Figure 10:
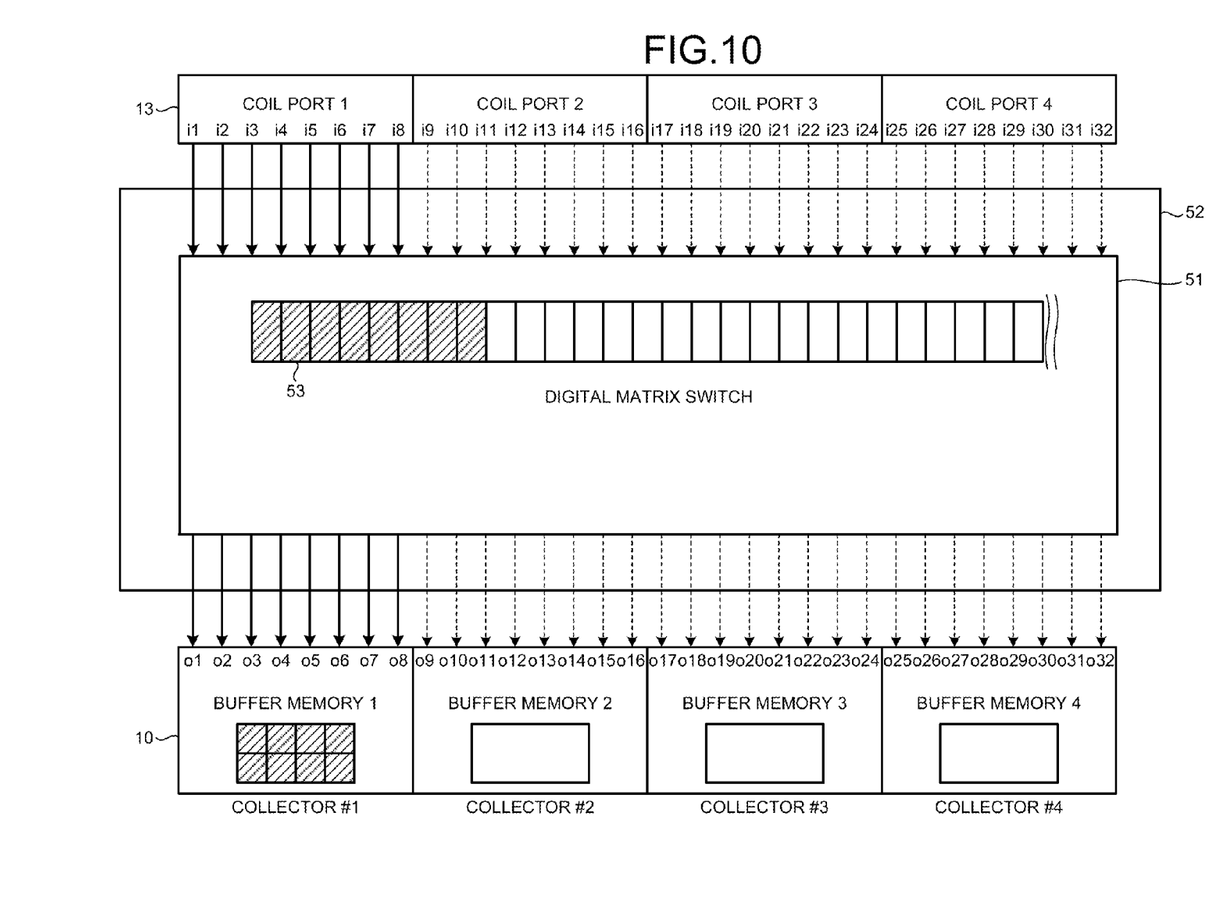
FIGS. 10 and 11 depict a configuration and a connection relation of a distribution substrate according to a third embodiment.
Figure 11:
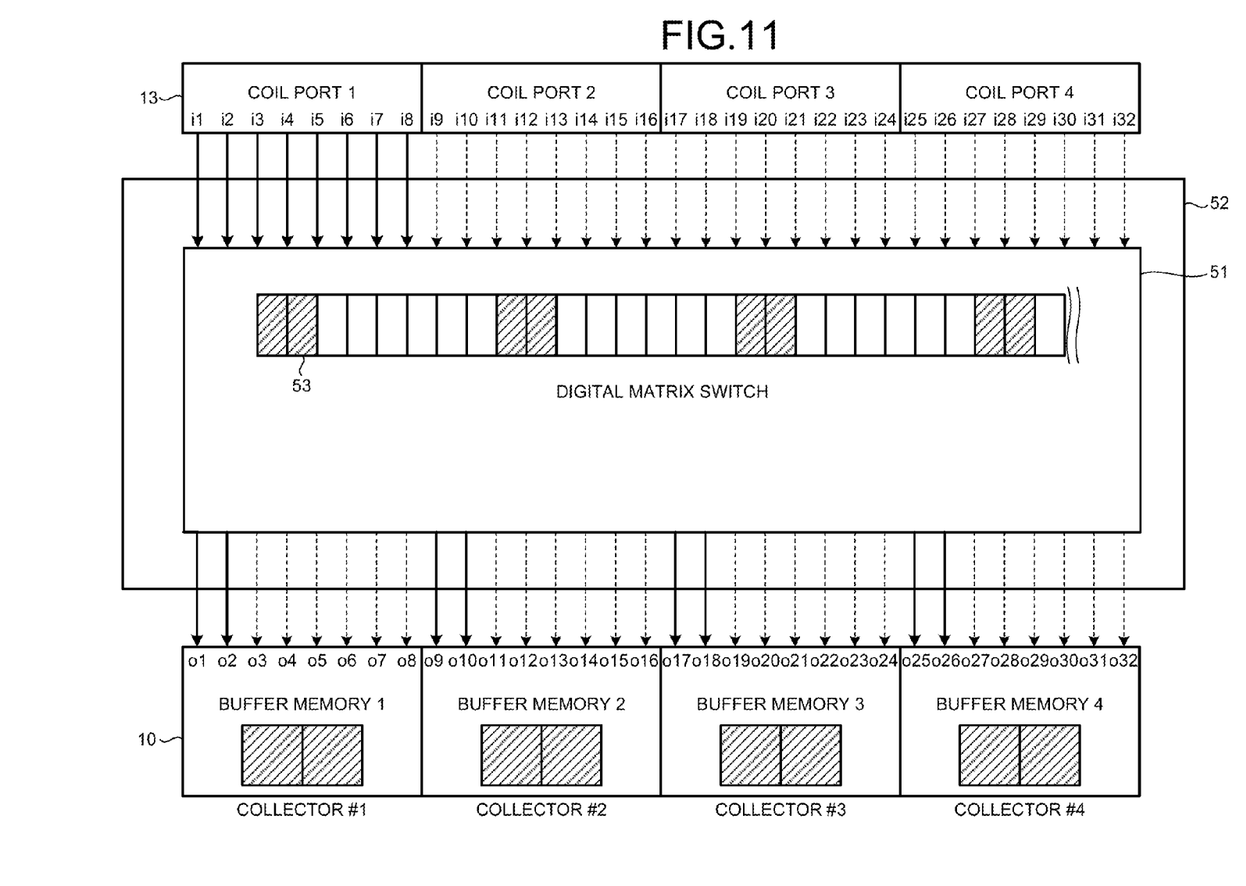

FIGS. 10 and 11 depict a configuration and a connection relation of a distribution substrate 52 according to the third embodiment. The distribution substrate 52 is placed between the coil ports 13 and the collectors 10 and distributes the magnetic resonance signal data generated with respect to channels by the A/D converter that is provided in each of the coil ports 13 to the collectors 10. The distribution substrate 52 can be installed on the couch 4 or on the gantry 12.

As shown in FIG. 10, for example, the distribution substrate 52 includes a digital matrix switch 51. The digital matrix switch 51 is controlled by the host computer 15. The distribution substrate 52 obtains information indicating which collector stores each of channels of the receiving coil in a buffer memory thereof, from the real-time sequencer 9 and switches a connection relation between output terminals i1 to i32 of the coil ports 13 (coil ports 1 to 4 shown in FIG. 10) to which the receiving coils are connected and input terminals o1 to o32 of the collectors 10 (collectors #1 to #4). The distribution substrate 52 is provided on, for example, the couch 4 or the gantry 12.

For example, a case where only output terminals corresponding to eight channels of the coil port 1 are used and output terminals of the coil ports 2 to 4 are not used is considered. Even in this case, the digital matrix switch 51 can connect the output terminals i1 to i8 of the coil port 1 to be distributed to the input terminals of the collectors #1 to #4 as shown in FIG. 11. For example, the output terminals i1 and i2 of the coil port 1 are connected to the input terminals o1 and o2 of the collector #1, the output terminals i3 and i4 of the coil port 1 are connected to the input terminals o9 and o10 of the collector #2, the output terminals i5 and i6 of the coil port 1 are connected to the input terminals o17 and o18 of the collector #3, and the output terminals i7 and i8 of the coil port 1 are connected to the input terminals o25 and o26 of the collector #4. Assuming, for example, that each of the collectors 10 includes a buffer memory of 2 gigabytes, a 1-gigabyte memory is allocated to one channel because two channels are allocated to each of buffer memories 1 to 4 of the collectors #1 to #4. As a result, raw data four times as much as a case where a connection relation between the output terminals i1 to i32 of the coil ports 13 and the input terminals o1 to o32 of the collectors 10 is fixed can be collected and thus a quadrupled imaging time can be realized with the same memory amount.

Figure 12:
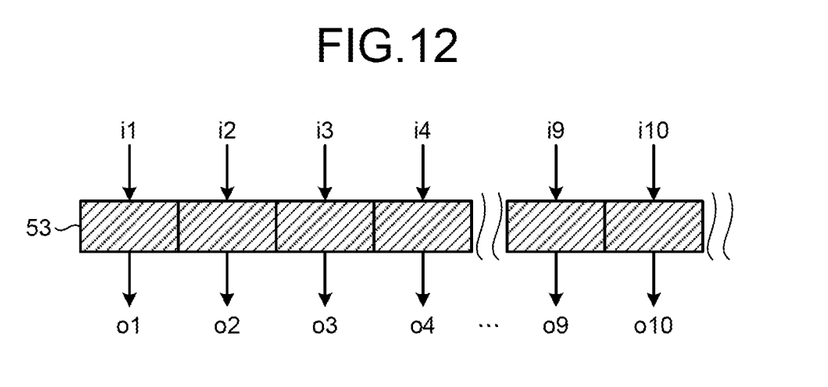
FIGS. 12 and 13 depict a configuration of a digital matrix switch according to the third embodiment.
Figure 13:
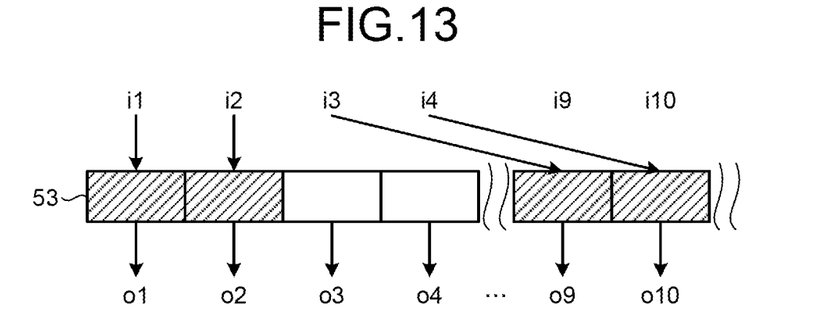

FIGS. 12 and 13 depict a configuration of the digital matrix switch 51 according to the third embodiment. The digital matrix switch 51 stores raw data output from the output terminals i1 to i32 of the coil ports 13 in a memory 53. The digital matrix switch 51 can specify memory areas in the memory 53 to which the output terminals i1 to i32 of the coil ports 13 are allocated, respectively, with a pointer.

FIGS. 12 and 13 also depict which output terminal of the coil ports 13 and which input terminal of the collectors 10 are allocated to each of the memory areas in the memory 53 of the digital matrix switch 51. FIG. 12 corresponds to FIG. 10 and depicts that memory areas are allocated to the output terminals i1 to i10 of the coil ports 13 and the input terminals o1 to o10 of the collectors 10, respectively. FIG. 13 corresponds to FIG. 11 and depicts a state where memory areas allocated to the output terminals i3 and i4 of the coil ports 13 are changed from memory areas allocated to the input terminals o3 and o4 of the collectors 10 to those allocated to the input terminals o9 and o10 of the collectors 10, respectively. With this configuration, more raw data can be collected than in the case where the connection relation of the output terminals i1 to i32 of the coil ports 13 and the input terminals o1 to o32 of the collectors 10 is fixed and a longer imaging time can be realized with the same memory amount.

As mentioned above, according to the third embodiment, the connection relation of the output terminals of the coil ports and the input terminals of the collectors is changed according to use situations of the channels of the receiving coil. With this configuration, which collector can store the collected magnetic resonance signal data in a buffer memory thereof can be controlled and the buffer memories of the collectors can be effectively used.

The first to third embodiments are explained above. According to the first to third embodiments, the preamplifier is provided in the receiving coil 6 and A/D conversion is performed at an earlier stage. Therefore, inclusion of noise in the magnetic resonance signal can be suppressed and performance degradation in the S/N ratio can be suppressed.

According to the first to third embodiments, the magnetic resonance signal is digitalized in the couch and therefore the thinning process or a serial-signal bundling process can be performed for the magnetic resonance signal data before the digitalized magnetic resonance signal data is output from the couch. Accordingly, the number of cables that connect the couch and the collectors can be reduced and a removable couch (also referred to as "dockable couch") that enables to move the subject remaining lying can be easily configured.

While the case where the ADCs for the direct sampling method are used is explained in the first to third embodiment, some of the ADCs can adjust the performance such as a data width or a sampling pitch. Accordingly, it is possible, for example, to determine a receiving coil to be used for imaging based on an imaging condition instructed by the operator and to use a different performance of the ADCs or a different gain at the later stage according to the determined receiving coil. For example, when a receiving coil used for imaging is one that receives the magnetic resonance signal from a narrow range such as a head receiving coil, the gain at the later stage can be controlled to be smaller than in a receiving coil that receives the magnetic resonance signal from a wider range such as a spine receiving coil or an abdomen receiving coil.

While the case where the A/D converter is provided in each of the coil ports on the couch or on the path from the receiving coil to each of the coil ports on the couch is explained in the first to third embodiments, the embodiments are not limited thereto. For example, when the coil ports are provided on the gantry, the A/D converter can be provided in each of the coil ports on the gantry. The A/D converter can be provided in the couch, not in the coil ports. In such a case, it is desirable that cables that connect the coil ports and the A/D converter are as short as possible to minimize an influence of noise.

According to at least one of the embodiments explained above, the A/D converter is provided in each of the coil ports or on the path from the receiving coil to each of the coil ports, so that inclusion of noise in the magnetic resonance signal can be suppressed with a simple apparatus configuration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
   a couch on which a subject is placed;
   a gantry that supports a static magnetic field magnet and a gradient coil;
   a receiving coil that receives a magnetic resonance signal emitted from the subject;
   a converter that converts a magnetic resonance signal output from the receiving coil into a digital signal, thereby generating magnetic resonance signal data; and
   a collector that collects the magnetic resonance signal data, wherein
   the couch or the gantry includes a coil port that connects the receiving coil and the collector to each other, and
   the converter is provided in the coil port.

2. The magnetic resonance imaging apparatus according to claim 1, wherein the converter has a function to convert the magnetic resonance signal into the digital signal by a direct sampling method, thereby generating the magnetic resonance signal data.

3. The magnetic resonance imaging apparatus according to claim 1, wherein
   the receiving coil outputs the magnetic resonance signal through a plurality of channels, and
   the converter converts the magnetic resonance signal into the digital signal with respect to each of the channels, thereby generating the magnetic resonance signal data.

4. The magnetic resonance imaging apparatus according to claim 3, wherein the converter includes a selector that selects magnetic resonance signal data of at least one channel from among the magnetic resonance signal data generated with respect to each of the channels.

5. The magnetic resonance imaging apparatus according to claim 3, wherein the converter includes a multiplexer that multiplexes the magnetic resonance signal data generated with respect to each of the channels.

6. The magnetic resonance imaging apparatus according to claim 3, wherein the converter includes an optical converter that converts the magnetic resonance signal data into an optical signal.

7. The magnetic resonance imaging apparatus according to claim 3, further comprising:
   a plurality of collectors; and
   a distribution digital matrix switch that distributes the magnetic resonance signal data generated with respect to each of the channels by the converter to the collectors, respectively.

8. The magnetic resonance imaging apparatus according to claim 1, wherein the couch is a mobile couch that can be attached to or detached from the gantry.

9. A couch that is provided in a magnetic resonance imaging apparatus, the couch comprising:
   a coil port to which a receiving coil that receives a magnetic resonance signal emitted from a subject is connected; and
   a converter that converts a magnetic resonance signal output from the receiving coil into a digital signal, wherein
   the converter is provided in the coil port.

* * * * *